US012295668B2

(12) United States Patent
Turgeman et al.

(10) Patent No.: US 12,295,668 B2
(45) Date of Patent: May 13, 2025

(54) SYSTEM FOR POSITION AND PROCESS VERIFICATION IN COMPUTER ASSISTED SURGERY

(71) Applicant: Mazor Robotics Ltd., Caesarea (IL)

(72) Inventors: Avi Turgeman, Beer Yaakov (IL); Moshe Shoham, Hoshaya (IL); Eli Zehavi, Tel-Aviv (IL)

(73) Assignee: Mazor Robotics Ltd., Caesarea (IL)

( * ) Notice: Subject to any disclaimer, the term of this patent is extended or adjusted under 35 U.S.C. 154(b) by 0 days.

(21) Appl. No.: 17/526,967

(22) Filed: Nov. 15, 2021

(65) Prior Publication Data

US 2022/0175462 A1 Jun. 9, 2022

Related U.S. Application Data

(60) Provisional application No. 63/122,296, filed on Dec. 7, 2020.

(51) Int. Cl.
*A61B 34/20* (2016.01)
*A61B 5/0205* (2006.01)
(Continued)

(52) U.S. Cl.
CPC ............ *A61B 34/20* (2016.02); *A61B 5/0205* (2013.01); *A61B 34/10* (2016.02); *A61B 34/25* (2016.02);
(Continued)

(58) Field of Classification Search
CPC ......... A61B 34/20; A61B 34/10; A61B 34/25; A61B 34/30; A61B 5/0205;
(Continued)

(56) References Cited

U.S. PATENT DOCUMENTS 6,381,485 B1  4/2002  Hunter et al.
7,974,677 B2  7/2011  Mire et al.
(Continued)

FOREIGN PATENT DOCUMENTS

CN  102988033  3/2013
CN  105361950  3/2016
(Continued)

OTHER PUBLICATIONS

"General Anesthesia." Mayo Clinic, Mayo Foundation for Medical Education and Research, Dec. 18, 2020, https://www.mayoclinic.org/tests-procedures/anesthesia/about/pac-20384568#:~:text=An%20anesthesiologist%20is%20a%20specially,functions%20and%20manages%20your%20breathing. (Year: 2020).*
(Continued)

*Primary Examiner* — Tammie K Marlen
*Assistant Examiner* — Megan T Fedorky
(74) *Attorney, Agent, or Firm* — Sheridan Ross P.C.

(57) ABSTRACT

Systems and methods for accurate determination of the position of an anatomic part of a subject in robotic assisted image-based surgery, using an inertial measurement unit (IMU) to determine the position and orientation of the anatomical part of the subject. The intrinsic drift of the IMU, which would make the IMU position measurements inaccurate, can be reset to zero regularly, at points of time when the subject's body is stationary. This can be achieved when motion from the subject's breathing and from the heartbeat are essentially zero. Such positions occur respectively when the respiratory signal shows the position of the breathing cycle to be at the end of the expiration phase, and the heartbeat signal represents a time in the diastole period of the subject's electrocardiographic cycle. When these two signal moments coincide, the IMU is essentially stationary, and its drift reset to zero.

20 Claims, 5 Drawing Sheets

(51) Int. Cl.
| | |
|---|---|
| *A61B 5/08* | (2006.01) |
| *A61B 17/00* | (2006.01) |
| *A61B 34/00* | (2016.01) |
| *A61B 34/10* | (2016.01) |
| *A61B 34/30* | (2016.01) |

(52) U.S. Cl.
CPC ........ *A61B 34/30* (2016.02); *A61B 2034/102* (2016.02); *A61B 2034/105* (2016.02); *A61B 2562/0219* (2013.01); *A61B 2562/028* (2013.01)

(58) Field of Classification Search
CPC ........ A61B 2034/102; A61B 2034/105; A61B 2562/0219; A61B 2562/028; A61B 2017/00703; A61B 2017/00725
See application file for complete search history.

(56) References Cited

U.S. PATENT DOCUMENTS

| | | |
|---|---|---|
| 8,092,457 B2 | 1/2012 | Oettinger et al. |
| 8,945,133 B2 | 2/2015 | Stein et al. |
| 9,226,799 B2 | 1/2016 | Lightcap et al. |
| 10,529,250 B2 | 1/2020 | Lehari |
| 2017/0132389 A1 | 5/2017 | McCaulley et al. |
| 2018/0103874 A1 | 4/2018 | Lee et al. |
| 2018/0199999 A1 | 7/2018 | Syverson et al. |
| 2019/0090955 A1 | 3/2019 | Singh et al. |
| 2019/0380791 A1 | 12/2019 | Fuerst et al. |
| 2019/0380794 A1 | 12/2019 | Al Jewad et al. |
| 2019/0388158 A1 | 12/2019 | Mahfouz |
| 2020/0250835 A1 | 8/2020 | Alzaga et al. |
| 2021/0093329 A1* | 4/2021 | Poltaretskyi .............. G09B 5/06 |

FOREIGN PATENT DOCUMENTS

| | | | |
|---|---|---|---|
| DE | 102011111671 A1 * | 2/2013 | ......... A61B 17/1622 |
| JP | 5192179 | 5/2013 | |
| JP | 5327458 | 10/2013 | |
| WO | WO 2015/087335 | 6/2015 | |
| WO | WO 2020/079596 | 4/2020 | |

OTHER PUBLICATIONS

Johns Hopkins Medicine: Day, Jo Ann. "Anesthesia for Orthopaedic Surgery: Sibley Memorial Hospital in Washington, D.C." Anesthesia for Orthopaedic Surgery | Sibley Memorial Hospital in Washington, D.C., 25 Jun. 25, 2020 (Year: 2020).*

Lee et al. "Automated motion artifact removal for intravital microscopy, without a priori information," Scientific Reports, Mar. 2014, vol. 4, No. 1, Article 4507, 9 pages.

Shechter et al. "Rest period duration of the coronary arteries: Implications for magnetic resonance coronary angiography," Medical Physics, Jan. 2005, vol. 32, No. 1, pp. 255-262.

International Search Report and Written Opinion for International (PCT) Patent Application No. PCT/IL2021/051449, dated Apr. 7, 2022, 21 pages.

* cited by examiner

SYSTEM FOR POSITION AND PROCESS VERIFICATION IN COMPUTER ASSISTED SURGERY

CROSS REFERENCE TO RELATED APPLICATIONS

This application claims priority to U.S. Provisional Application No. 63/122,296, filed on Dec. 7, 2020, and entitled "SYSTEM FOR POSITION AND PROCESS VERIFICATION IN COMPUTER ASSISTED SURGERY", the entirety of which is hereby incorporated by reference.

FIELD

Embodiments of the present disclosure relate to the field of orthopedic surgery, especially for use in accurate determination of the position of an orthopedic anatomic part of a patient.

BACKGROUND

The success of computer and robotic assisted image-based surgery is dependent on accurate registration between pre-operative images of the region of interest and the intra-operative surgical field. Precision of registration is of paramount importance, as in a robotic surgical system, the entire surgical process depends on accurately identifying anatomical features in the patient that correspond to those identified in the preoperative images, upon which the operation was planned. Obviously, accurate registration should be maintained throughout the entire surgical process to retain the fidelity of the robotic movements. However, after the initial registration, the patient may move, and internal anatomical structures may shift relative to each other. Hence, it is crucial to monitor intraoperatively in order to detect potential displacement of anatomical features in the region of interest following the initial registration. Thus, while accurate registration is essential to define the pose of the surgical tools relative to the pre-operative plans, intra-operative real-time monitoring of the surgical process is of equal importance.

Different systems, using a variety of equipment and alignment methods, have been developed to ensure proper registration during surgical procedures, despite motion of the patient. Several representative examples include:
U.S. Pat. No. 6,381,485 for "Registration of human anatomy integrated for electromagnetic localization", assigned to Medtronic Navigation, Inc. Some methods disclosed therein involve placing, activating, and detecting magnetic field sensors to generate a displaced image data set, and generating a display based on the displaced image data set.
U.S. Pat. No. 7,974,677 for "Method and apparatus for preplanning a surgical procedure", also assigned to Medtronic Navigation, Inc., which discloses, inter alia, a method and system to assist in a selection and planning of a procedure and assists in selecting a prosthetic for the procedure. Generally, in those embodiments the system allows for image acquisition of a selected area of the anatomy. A model may be formed of the anatomy from the acquired images. The system may also allow for navigational tracking of the procedure to ensure that the procedure is substantially carried out relative to the selected plan.

Further systems for achieving intra-operative registration have been described in the following patent applications:
WO 2015/087335 for "Semi-Rigid Bone Attachment Robotic Surgery System", and
WO 2020/079596 for "Versatile Multi-Arm Robotic Surgical System", both having common inventors with the present application, and
U.S. Pat. No. 9,226,799 for "Inertially Tracked Objects" to C. Lightcap et al.

The disclosures of each of the publications mentioned in this section and in other sections of the specification, are hereby incorporated by reference, each in its entirety.

SUMMARY

Embodiments of the present disclosure provide new exemplary systems for improving accuracy of the registration process intraoperatively in real time. Such exemplary implementations detect position and orientation changes following the initial registration process, and at the same time monitor and verify that the surgical process proceeds as planned. The systems use inertial measurement units (IMU) to define the position and orientation of the anatomical part of interest.

An inertial measurement unit (IMU) is an electronic device that measures and reports orientation, velocity, and gravitational forces through the use of accelerometers and gyroscopes, and optionally, also magnetometers. IMUs are the base component of the inertial navigation systems used in a variety of mobile devices or platforms for navigation, stabilization, and path correction, computational system control; and mobile mapping. The data collected by an IMU are processed to track position through a process called dead reckoning. In an inertial navigation system, the data collected by an IMU is used to calculate current position of the device to which it is attached. Combining this logic with a system of maps, can show where the unit is located relative to a map. Thus, it operates in a manner similar to the use of a Global Positioning System (GPS) tracking system, but without the need to be connected to or in communication with any remote navigational system. In the case of the methods of the present disclosure, the IMU can show its position relative to a preoperative medical image set, or intraoperative images.

IMUs require precise accelerometers and gyroscopes, and it is the accuracy thereof that impacts the overall performance of the inertial sensor system. A gyroscope in an IMU may be based on several principles, such as mechanical, gas-bearing, ring laser, or fiber optics. Some gyroscopes, such as mechanical and gas-bearing, are based on the conservation of angular motion. Fiber optic gyroscopes are based on measurement of light from two different directions. These provide extremely precise rotational rate information due to their lack of moving parts but are larger, more expensive, and have higher power demands.

Micro-electromechanical systems (MEMS) technology can be used to produce very small accelerometers and other motion detection sensors. The principle of this technology is to combine basic mechanical parts and tools with integrated circuit silicon technology, such as that found in computer processors. The resulting miniaturization enables a micro-fabricated electronic chip that fits multiple sensors in a small space. Using the technology of MEMS allows the construction of a miniature MEMS IMU, which incorporates accelerometers, angular motion sensors and magnetic sensors in a small package, and having a high degree of accuracy. Such a miniature IMU attached to a bone on which the operation is being performed, and optionally on the tool performing the operation, would greatly simplify the performance of robotic surgical processes, by providing direct information about the bone pose and optionally the tool pose, relative to the surgical plan images.

Embodiments of the present system are based on use of such a small MEMS IMU, connected to the anatomy, such as a vertebra, or to a k-wire or similar element, which is attached to a solid anatomical feature in the region of surgical interest. Though the methods and systems of the present disclosure can be used for following the movement of any anatomical feature, the method is especially useful for monitoring drilling procedures performed on vertebrae, and that example is widely used throughout this disclosure to illustrate the methods and systems proposed. However, such use of the vertebral examples used is in no way intended to limit the disclosure to vertebral applications. Using its internal motion and position measurement capability, the MEMS IMU is able to directly and conveniently measure the absolute position and orientation of the vertebra, and hence also to track its motion. This can be provided to the system controller, thus enabling the controller to adapt the position of a surgical tool attached to a robotic arm to follow changes in the position and orientation of the vertebra, without the need for other tracking modalities, which may need line of sight contact with the vertebra or a marker attached thereto, such other navigation methods being prone to disturbance during the motion of personnel or the robot arms during surgery.

However, a major problem with IMUs in general, and with MEMS IMUs in particular, is the inherent drift in both distance (linear motion) and angle (angular motion), which precludes the collection of accurate measurements over a lengthy period of time. IMU tracking systems can introduce significant error through drift. Each pose output from the IMU tracking system, is calculated from the previously determined pose, to which is added the changes in pose calculated from the measured changes in acceleration and angular rate, without reference to any external references. Consequently, the errors of the tracking process are cumulative such that the error in each new estimated IMU pose grows with time. Specifically, the inertial tracking system integrates the linear accelerations and angular velocities provided by the IMU to calculate the new IMU pose. Such integrations, and even double integrations for the acceleration measurements, may introduce inaccuracies, and these accumulated error leads to drift, which presents itself as an ever-increasing difference between where the inertial tracking system thinks the IMU is located and where the actual IMU is. If the drift is not compensated for, the pose of the tracked object, such as a vertebra to which the IMU is attached, can be incorrectly predicted based on the difference between the predicted IMU pose and the actual IMU pose. This could cause the surgical system to be improperly configured, which could lead to inaccuracies in the execution of the surgical plan, with possible dangerous results.

This limitation in accuracy because of drift of the reference position of the IMU must be overcome in order to ensure adequate accuracy of the position information obtainable from the IMU control unit. In general use, the problem of IMU drift can be readily overcome by docking the IMU at a known static location at regular intervals, and resetting the IMU output to that base reference position, thereby cancelling out any accumulated drift. However, such solutions are not easily applied for use with an IMU attached in a fixed position to the vertebra of the patient.

According to an exemplary method described in the present disclosure, a method of compensating such IMU drifts can be achieved by periodically resetting the IMU to its zero reference point at times when it is determined that the patient is stationary, thus enabling the offsetting of the accumulated drift at those times. However, even when anesthetized, the patient undergoes movements, such as from his/her breathing, and from his/her pulse, such that the position of the IMU when attached to the patient's body cannot be generally considered to be a stationary reference position.

This problem is overcome in the systems and methods described in the present disclosure, by defining a specific physiological moment which provides an essentially stationary and repeatable position of the subject's body, such that an IMU attached to a point on or in the patient's body, can use that stationary position for periodic resetting of the drift in the IMU. The stationary position used in this disclosure is a point in time when the end-of-expiration point of the patient's breathing cycle coincides with the diastole period of the heart. In operations where the patient is under general anesthesia, respiratory rate is controlled by the anesthesiologist using settings on the respirator providing breathing support to the patient. At the end of the expiration phase, the lungs are temporarily stationary, before the next inhalation phase begins. With regard to heart function, during the diastole period, the heart is relaxed and hence in a temporary stationary state. Therefore, by selecting points in time during which end-of-expiration coincides with diastole, the body is essentially stationary and therefore, an IMU attached to the body has essentially zero velocity, and, assuming that the patient, or at least the attachment point, has not physically moved, the IMU has zero translational and orientational displacement from its previous "stationary" position. Since the respiratory cycle under anesthesia is about 12 breaths per minute, corresponding to one breathing cycle every 5 seconds, and heart beat rate is about 60-70 beats per minute or approximately 1 per second, of which approximately half of each cycle corresponds to diastole, it is possible to reset the IMU velocity and position drift approximately once every 5 seconds. Therefore, the maximal drift that can be accumulated can be compensated for by resetting the zero reference of the IMU every 5 seconds, if deemed necessary.

To provide some quantitative perspective to the performance of the type of systems disclosed in the present application, it is noted that the commonly used MEMS IMU-HGuide i300, as provided by Honeywell International Inc. of Charlotte, NC 28202, weighs only 35 g, and has a volume of ~17 $cm^3$ (2.5 cm×2.5 cm×2.75 cm) making such a device convenient for mounting on an anatomic part of a patient during surgery. It has, according to its specification limits, a drift of 0.3 degree/hour in rotation and 0.02 mg in acceleration. Thus, over the 5 seconds, at which point of time, a drift reset may be applied, this drift can reach 0.00042 degree, which is well within the accuracy limit desired for orientation needed during robotic surgery, and 2.5 mm., which is acceptably within the boundary limits of positional accuracy needed during robotic surgery, such that, so long as the IMU drift is reset to zero at the 5 second intervals proposed, such systems are adequate for such requirements. Moreover, it is expected that as MEMS IMUs continue to develop, devices with less drift will be achieved, which will make them suitable even for more delicate surgical operations.

In surgical applications performed using the MEMS IMU system of the present disclosure, the position of the surgical tool too can be tracked by means of an IMU attached to the tool holder. This is in addition to the position of a bone on which the surgical procedure is being performed, by means of the IMU attached to the bone. Consequently, the complete surgical process can be tracked, additional to positional information provided by the robotic system, and without the need for remote navigational system tracking. Tracking of the body part or bone being operated on is important since that part may move as a result of the surgical procedure being performed on it.

The last mentioned example may be important since drilling into a vertebra for pedicle screw implantation may cause the vertebra to move or tilt due to the torque applied by the drill on the bone. This motion or tilt is a function of the outside force applied to the bone, as well as the properties of the bone into which the drill is penetrating, such as bone density. The density varies in different bones and in specific regions within a given bone. In the vertebra, the outer cortical bone is denser than the cancellous bone inside of the pedicles and vertebral bodies; thus, if the drilling angle is such that it may cause the vertebra to tilt, drilling through cortical bone would tend to cause a greater tilt of the bone than drilling through cancellous bone, which has less resistance. A MEMS IMU attached to the vertebra is able to accurately detect vertebral tilt, which varies as the drill bit passes from the denser cortical bone through the cancellous bone. As the drilling proceeds, the tilt can be measured and compared to known standard expected tilts for pedicle drillings. By following the changes in tilt, it is thus possible to detect when the drill is passing through cortical bone, when it is has traversed from cortical bone into cancellous bone, and again entered the cortical bone. As the tilt changes during the drilling process, is thus possible to detect entry into the cortical bone on the anterior side of the vertebral body, and to set the robot to stop drilling when it reaches the rim of cortical bone on the anterior aspect of the vertebra. Using the IMU to monitor the tilt during drilling, can therefore enable the tracking of the drill position during its progress through a vertebra.

This torque detection process is generally possible only with robot-guided drilling, since robotic drilling advances the drill accurately along the planned straight trajectory without causing lateral forces. In manual drilling, the generation of lateral forces may considerably alter the applied torque, thus invalidating or obscuring the accurate relationship between measured tilt and bone density.

Further, the drilling process generates vibrations that can be detected by the MEMS IMU system. These vibrations have different frequencies as the drill passes from cancellous to cortical bone and vice versa. Patterns of vibrations and displacement as the drill passes through the pedicle and the vertebral body are measured by the MEMS IMU. These patterns can then be compared to those expected by the surgical plan, thus monitoring and verifying the expected trajectory of the drill or other surgical tool.

In order to best detect displacement and vibration of the vertebra or other bony structure, the position of the MEMS IMU should be optimized for detection of both displacement in any direction and vibrational frequencies. For a MEMS IMU positioned on a vertebra via a K-wire, the optimal location will also include a consideration of the mechanical properties of the K-wire. Low frequency motion due to drill-applied torque and high frequency vibrations might require two different optimal locations of the MEMS IMU. For low frequencies and in the steady state, a more distant location from the vertebra might be better, while resonance points along the K-wire might be best for high frequency vibrations. Therefore, the optimal location is defined as being able to satisfy both requirements. Alternatively, several MEMS IMUs might be attached to the anatomy in different locations, or one may be implanted at each expected resonance position in order to further optimally cover all frequencies. Additionally, it is to be understood that since the motion of neighboring vertebrae are not necessarily correlated, in surgical procedures where more than one vertebra is to be operated on, separate IMUs may be needed for each vertebra.

The IMU will also detect movements of the patient him/herself, unrelated to the physiological movements arising from breathing and heartbeat, such as sneezing or whole body movements. Similarly, there may occur more significant movements of the bone on which the operation is being performed such as by the manipulating of the bone by the surgeon. Since the IMU cannot intrinsically distinguish such larger movements from the small movements arising, for instance, from the actions of the surgical tool, it is necessary for the controller to differentiate between movements being monitored by the IMU arising from (i) the small physiological breathing or heartbeat motions, or from small movements of the bone from the surgical tool action, and (ii) gross movements of the bone due to motion of the subject's whole body, or because of surgical movement of the body or body part. In the case of such large movements, it is necessary to perform a new registration of the subject to the robotic co-ordinate frame of reference, to ensure that the robot now relates to the new position of the subject or the bone on which the surgical plan is being performed. Such a differentiation can be achieved by defining a motion threshold which differentiates between the magnitude of movements expected from (i) either the breathing and heartbeat of the subject or the expected small movements of the bone under the effect of the surgical tool, both of which have a small magnitude, and (ii) unexpected movements arising from patient self-movement or movement by the medical personnel or the surgeon, which will be substantially larger in magnitude than the physiological or surgical movements.

There is thus provided in accordance with an exemplary implementation of the devices described in this disclosure, a surgical robotic system comprising:

(a) an inertial measurement unit (IMU) configured to connect to an anatomical feature of a subject; and (b) a system controller, the system controller adapted to:
  (i) receive a respiratory signal corresponding to a respiratory cycle of the subject, and a heartbeat signal corresponding to the heartbeat cycle of the patient;
  (ii) determine at least one point in time when the respiratory signal represents a position of minimal motion of the subject arising from the respiration of the subject, and the heartbeat signal simultaneously represents a position of minimal motion of the subject arising from the heartbeat of the subject; and
  (iii) generate an instruction to reset at the at least one point in time, drift detected at that at least one point in time in the pose determination of the IMU.

In such a system, the at least one point in time when the respiratory signal represents a position of minimal breathing motion of the subject may be selected by the controller to be at the end of the expiration phase of the subject's breathing cycle. Furthermore, the at least one point in time when the heartbeat signal represents a position of minimal pulse motion of the subject, is selected by the controller to be the diastole period of the subject's electrocardiographic cycle.

Additionally, in any such systems, the controller may be configured to generate an instruction to reset the drift of the IMU at at least one point in time when the end of the expiration phase and the cardiac diastole period temporally coincide. In such a case, the frequency of temporal coincidences of the end of expiration phase and the cardiac diastole period, at which the controller is adapted to reset the drift of the IMU, may be determined by the level of drift of the IMU. Furthermore, the controller may be adapted to reset the drift of the IMU at every incidence of the temporal coincidence of the end of expiration phase and the cardiac diastole period.

According to yet further implementations of such systems, the IMU may a microelectromechanical (MEMS) based unit.

In any of the above described systems, the IMU may be attached fixedly to an anatomic feature of the subject, such that the controller detects changes in at least one of the orientation or position of the anatomical feature of the subject. In such a system, the anatomical feature may be a bone of the subject, and the controller may then be adapted to use the changes in at least one of orientation or position of the bone to determine a type of bone through which a surgical tool is passing. The controller may then be adapted to determine the position in the bone of a surgical drill performing a drilling action on the bone, according to the type of bone disclosed. Furthermore, the controller may be adapted to instruct the performance of a new registration of the robot to the subject if the detected changes in at least one of the orientation or position of the anatomical feature of the patient, exceed respective predetermined threshold levels.

There is also provided according to further implementations of the above described systems, a system such as those described above, in which the IMU is connected to a bone of the subject using a K-wire. The IMU may be connected to the K-wire in a region which maximizes the amplitude of vibrations arising from a drilling process into the bone. Furthermore, the frequency of vibrations detected by the IMU may provide an indication of the type of bone through which the surgical tool generating those vibrations is passing, higher frequency vibrations being interpreted by the controller as indicating passage of the surgical tool through cortical bone, and lower frequency vibrations being interpreted by the controller as indicating passage of the surgical tool through cancellous bone. In such cases, the controller may be adapted to use the type of bone indicated, to determine the position in the bone of a surgical drill performing a drilling action on the bone.

Any of the above described systems using a K-wire may further comprise a second IMU attached to the K-wire, wherein one IMU is attached in a region at which the higher frequency vibrations expected from drilling in cortical bone are maximized, while the second IMU is located in a region where the lower frequency vibrations expected from drilling in cancellous bone are maximized.

According to yet further exemplary embodiments of the presently described systems, the controller may be adapted to compare the indicated position of the drill relative to a bone through which it is passing, with the position of the drill relative to a bone through which it is passing expected from the surgical plan, to verify whether the surgical procedure is proceeding according to the surgical plan.

Additionally, in any of the above described systems, if the respiratory cycle arises from a subject under general anesthesia, the end of the expiration stage of the subject's breathing cycle should be determined by an anesthesiologist.

According to yet another implementation, any of the above described systems may further comprise a further IMU configured to connect to the surgical tool, such that the pose of the surgical tool relative to the anatomical feature of the subject may be determined.

There is further provided according to an exemplary implementations of methods of the present disclosure, a method of monitoring a surgical robotic execution of a surgical plan performed on an anatomical feature of a subject, comprising:

(i) using a drift-corrected inertial measurement unit (IMU) attached to the anatomical feature of the subject, determining an initial pose of the anatomical feature in the co-ordinate system of the IMU;

(ii) commencing the surgical robotic procedure and repeating the determination of the pose of the anatomical feature at intervals during the course of the surgical robotic procedure; and (iii) if the IMU indicates that the pose of the anatomical feature has changed by more than a predetermined amount, performing a new registration of the surgical robot co-ordinate system to the preoperative surgical plan.

Such a method may further comprise the step of using the change in the pose of the anatomical feature to determine the interaction of a surgical tool of the surgical robot with the anatomical feature. In such a method, if the anatomical feature is a bone of the subject, the method may further comprise the step of determining the type of bone tissue through which the surgical tool is passing, by using the change in the pose of the anatomical feature.

According to yet further methods, the new registration of the co-ordinate system of the surgical robot to the preoperative surgical plan, should reflect the changed position of the anatomical feature of the subject in the co-ordinate system of the surgical robot.

In any of the above described methods, the IMU drift correction may be achieved by resetting the zero reference position of the IMU at a point in time when a respiratory signal corresponding to the end-exhalation phase of the subject's breathing cycle, and a heartbeat signal corresponding to the diastole period of the subject's electrocardiograph signal, temporally coincide.

It is to be understood that throughout this disclosure, and as claimed, references to the resetting of the IMU, or resetting the drift of the IMU, or resetting the IMU output, or zeroing the drift of the IMU, or similar expressions, are all intended to refer to the process in which any accumulated drift in the zero base reference point of the IMU is reset to the zero value of the IMU, so that the IMU measurements relate to a known base reference value.

Example aspects of the present disclosure include:

A surgical robotic system comprising: an inertial measurement unit (IMU) configured to connect to an anatomical feature of a subject; and a system controller, the system controller adapted to: (i) receive a respiratory signal corresponding to a respiratory cycle of the subject, and a heartbeat signal corresponding to the heartbeat cycle of the patient; (ii) determine at least one point in time when the respiratory signal represents a position of minimal motion of the subject arising from the respiration of the subject, and the heartbeat signal simultaneously represents a position of minimal motion of the subject arising from the heartbeat of the subject; and (iii) generate an instruction to reset at the at least one point in time, drift detected at that at least one point in time in the pose determination of the IMU.

Any of the aspects herein, wherein the at least one point in time when the respiratory signal represents a position of minimal breathing motion of the subject is selected by the controller to be at the end of the expiration phase of the subject's breathing cycle.

Any of the aspects herein, wherein the at least one point in time when the heartbeat signal represents a position of minimal pulse motion of the subject is selected by the controller to be the diastole period of the subject's electrocardiographic cycle.

Any of the aspects herein, wherein the controller is configured to generate an instruction to reset the drift of the IMU at at least one point in time when the end of the expiration phase and the cardiac diastole period temporally coincide.

Any of the aspects herein, wherein the frequency of temporal coincidences of the end of expiration phase and the cardiac diastole period, at which the controller is adapted to reset the drift of the IMU, is determined by the level of drift of the IMU.

Any of the aspects herein, wherein the controller is adapted to reset the drift of the IMU at every incidence of the temporal coincidence of the end of expiration phase and the cardiac diastole period.

Any of the aspects herein, wherein the IMU is a microelectromechanical (MEMS) based unit.

Any of the aspects herein, wherein the IMU is attached fixedly to an anatomic feature of the subject, such that the controller detects changes in at least one of the orientation or position of the anatomical feature of the subject.

Any of the aspects herein, wherein the anatomical feature is a bone of the subject, and the controller is adapted to use the changes in at least one of orientation or position of the bone to determine a type of bone through which a surgical tool is passing.

Any of the aspects herein, wherein the controller is adapted to determine the position in the bone of a surgical drill performing a drilling action on the bone, according to the type of bone disclosed.

Any of the aspects herein, wherein the controller is adapted to instruct the performance of a new registration of the robot to the subject if the detected changes in at least one of the orientation or position of the anatomical feature of the patient, exceed respective predetermined threshold levels.

Any of the aspects herein, wherein the IMU is connected to a bone of the subject using a K-wire.

Any of the aspects herein, wherein the frequency of vibrations detected by the IMU provides an indication of the type of bone through which the surgical tool generating those vibrations is passing.

Any of the aspects herein, wherein higher frequency vibrations are interpreted by the controller as indicating passage of the surgical tool through cortical bone, and lower frequency vibrations are interpreted by the controller as indicating passage of the surgical tool through cancellous bone.

Any of the aspects herein, wherein the controller is adapted to use the type of bone indicated, to determine the position in the bone of a surgical drill performing a drilling action on the bone.

Any of the aspects herein, wherein the IMU is connected to the K-wire in a region which maximizes the amplitude of vibrations arising from a drilling process into the bone.

Any of the aspects herein, further comprising a second IMU attached to the K-wire, wherein one IMU is attached in a region at which the higher frequency vibrations expected from drilling in cortical bone are maximized, while the second IMU is located in a region where the lower frequency vibrations expected from drilling in cancellous bone are maximized.

Any of the aspects herein, wherein the controller is adapted to compare the indicated position of the drill relative to a bone through which it is passing, with the position of the drill relative to a bone through which it is passing expected from the surgical plan, to verify whether the surgical procedure is proceeding according to the surgical plan.

Any of the aspects herein, wherein, if the respiratory cycle arises from a subject under general anesthesia, the end of the expiration stage of the subject's breathing cycle is determined by an anesthesiologist.

Any of the aspects herein, further comprising an IMU configured to connect to the surgical tool, such that the pose of the surgical tool relative to the anatomical feature of the subject may be determined.

A method of monitoring a surgical robotic execution of a surgical plan performed on an anatomical feature of a subject, comprising: using the registration of the co-ordinate system of a surgical robot to a preoperative surgical plan, aligning the surgical robot such that the surgical procedure can be performed on the anatomical feature of the subject; using a drift-corrected inertial measurement unit (IMU) attached to the anatomical feature of the subject, determining an initial pose of the anatomical feature in the co-ordinate system of the IMU; commencing the surgical robotic procedure and repeating the determination of the pose of the anatomical feature at intervals during the course of the surgical robotic procedure; and if the IMU indicates that the pose of the anatomical feature has changed by more than a predetermined amount, performing a new registration of the surgical robot co-ordinate system to the preoperative surgical plan, such that the surgical procedure can be continued on the anatomical feature of the subject at its changed pose.

Any of the aspects herein, further comprising the step of using the change in the pose of the anatomical feature, to determine the interaction of a surgical tool of the surgical robot with the anatomical feature.

Any of the aspects herein, wherein the anatomical feature is a bone of the subject, the method further comprising the step of determining the type of bone tissue through which the surgical tool is passing, by using the change in the pose of the anatomical feature.

Any of the aspects herein, wherein the new registration of the co-ordinate system of the surgical robot to the preoperative surgical plan is performed to reflect the changed position of the anatomical feature of the subject in the co-ordinate system of the surgical robot.

Any of the aspects herein, wherein the IMU drift correction is achieved by resetting the zero reference position of the IMU at a point in time when a respiratory signal corresponding to the end-exhalation phase of the subject's breathing cycle, and a heartbeat signal corresponding to the diastole period of the subject's electrocardiograph signal, temporally coincide.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1-X_n$, $Y_1-Y_m$, and $Z_1-Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

Embodiments of the present disclosure will be understood and appreciated more fully from the following detailed description, taken in conjunction with the drawings in which.

DETAILED DESCRIPTION

Figure 1:
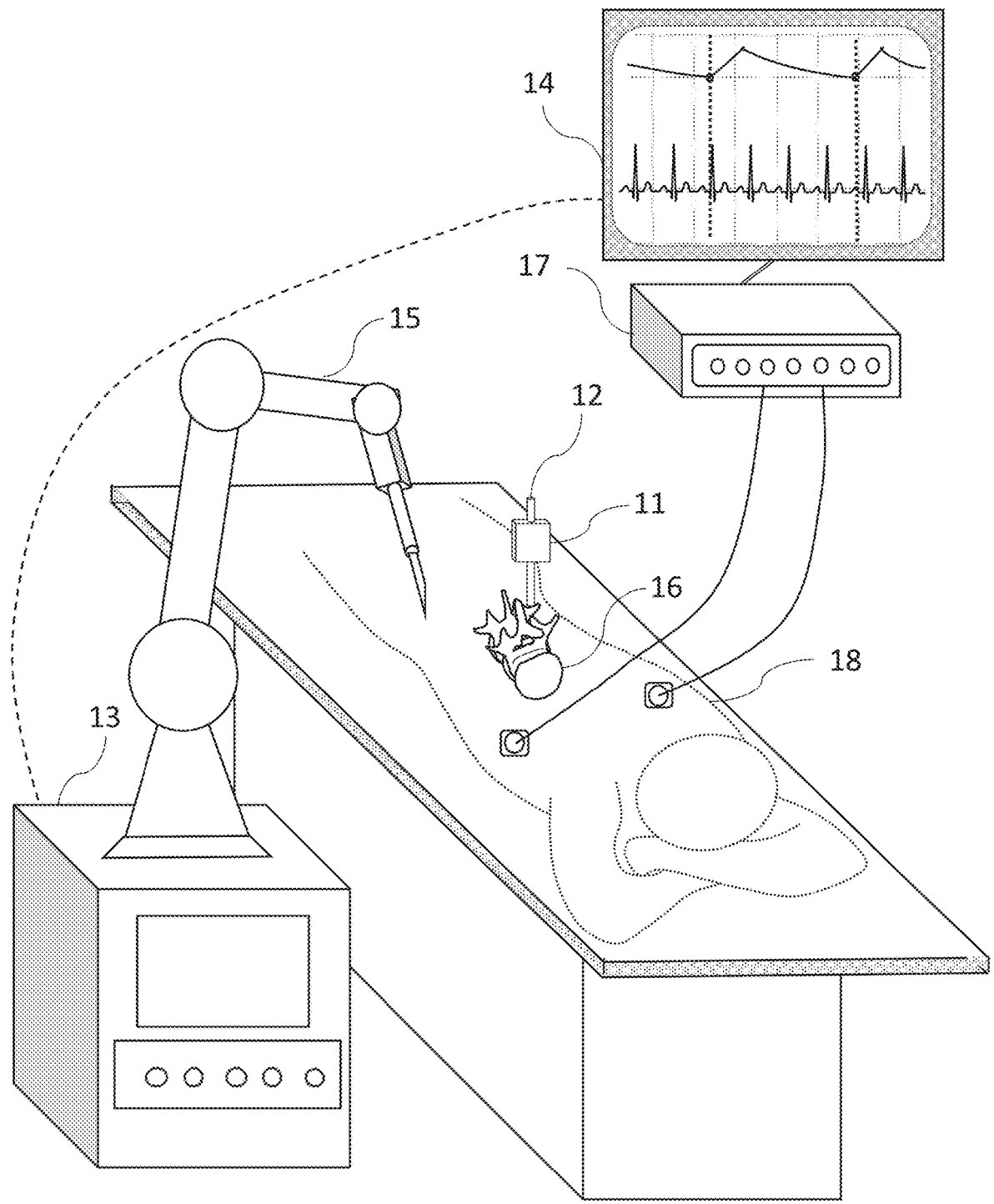
FIG. 1 shows an exemplary IMU system configuration for performing the methods described in the present disclosure.

Reference is first made to FIG. 1, which illustrates schematically an exemplary system according to the present disclosure, using an IMU 11 attached to a vertebra of a subject 18 undergoing spinal surgery. A robotic arm 15 of a surgical robot is used to carry out a surgical procedure on a vertebra 16 of a patient 18 under the direction of a system control unit 13. A MEMS IMU 11 is fixedly attached to the vertebra 16 upon which, or adjacent to which, the robotic arm 15 is to operate. The IMU 11 may be attached to the bone via a K-wire 12 or any other stable structure. The IMU enables continuous tracking of the position and orientation of the vertebra, which can be provided to the system controller, thus enabling the controller to adapt the position of the operation of the robotic arm 15 to follow changes in the position and orientation of the vertebra, without the need for other tracking modalities.

In order to contend with any drift in the IMU, the current system includes a physiological monitoring and processing device 17 to monitor the pulse and respirations of the patient 18, using electrodes for the EKG tracing, and a breath sensor (not shown) for analyzing the breath cycle of the patient. The EKG data and the respiratory data of the patient, may be recorded or processed by the physiological monitoring device 17, which should be in electronic communication with the system control unit 13. The breathing and pulse data may be displayed on a monitor 14. The system controller 13 or the physiological monitoring device 17 analyze the data and identifies areas in which the patient's lungs and heart are both in their resting position, which can then be used as a stationary position for resetting the IMU drift to zero, as further explained hereinbelow in FIG. 2. It is to be understood that the way in which the control and monitoring units handle and analyze the data of the methods and systems described in the present disclosure are intended to be only one possible non-limiting configuration, and that alternative combinations or arrangements of receiving and analyzing the data are also intended to be covered by this exemplary description.

Figure 2:
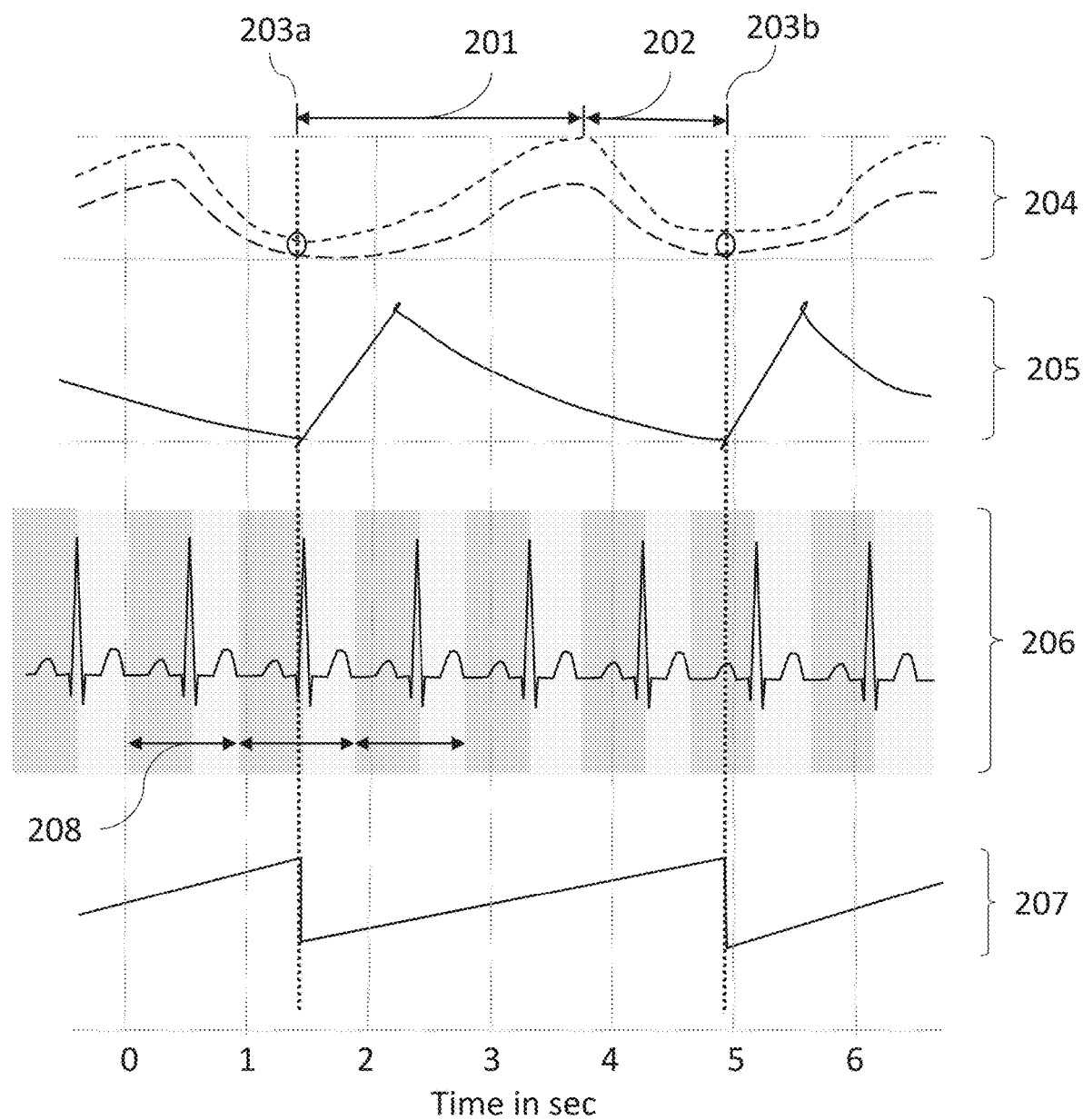
FIG. 2 illustrates the aligned traces of a typical respiratory pattern, a typical EKG trace with superimposed systole and diastole, and time points corresponding to coincidence of end expiration with diastole, at which point reset of the IMU may be performed.

Reference is now made to FIG. 2, which illustrates examples of output traces of patient data from the monitoring device 17 shown in FIG. 1, and how this information can be used for determining the correct timing points for resetting the accumulated drift of the MEMS IMU 11. The units of measurement for the x-axis, for all traces, is time in seconds. The top traces 204 show the breath cycles of the subject for two representative inspiratory-expiratory cycles, as could be measured, for instance, by the air pressure at the subject's oral/nasal cavities, typically at a breathing mask. The upper dotted line and the lower dotted line show the normal extent of variation in a typical respiratory cycle for a person breathing spontaneously. The period 201 represents the inhalation phase, and the period 202 represents the exhalation or expiration phase. The circles at the nadir of each cycle represent the end of expiration in the breath cycle. At these end-of-exhalation points, the lungs have emptied and the rib cage has come to rest after exhalation and before the beginning of inspiration for the following breath. Thus, at that moment, no motion is generated by expansion and contraction of the rib cage, and hence, of other associated body parts, such as the spine.

Trace 205 represents a typical inspiratory and expiratory pattern of a subject, either under general anesthesia or otherwise unconscious, who is being ventilated automatically by a respirator. As is observed, the overall shape of the breathing cycle is somewhat different from that of natural breathing, but also in this situation, there is a point of time at the transit between the end of the natural exhalation of the subject, and the beginning of the forced inspiration phase, at which the lungs and hence the body of the subject is stationary. The timing of each breath is controlled by the respirator, which can be modulated by an anesthesiologist or other health care professional. The automation of the inspiratory-expiratory cycle provides the opportunity for precise timing of each breath.

Trace 206 illustrates a representative electrocardiogram (EKG) trace of the same subject whose respirations are recorded in traces 205 or 204. The EKG measures electrical correlates of the cardiac pumping cycle, as recorded from skin electrodes. The cycles of systole (ventricular contraction) and diastole (ventricular relaxation) are represented by the time indicated by the arrows 208, the lighter shaded segments representing systole and the intervening dark segments representing diastole. During diastole, any motion of the patient's body caused by the pumping action of the heart is paused. The monitoring device provides the respiratory and cardiac information to the control system, which analyzes the data to identify points of time at which end expiration coincides with diastole, represented by lines 203a and 203b in FIG. 2. At these points of time, the system registers an opportunity to reset the MEMS IMU output signal to zero, thereby compensating for the accumulated the drift history since the last drift reset. Unlike the natural breathing cycle of traces 204, 206, the forced ventilation cycle of trace 205 shows a sharp transition from exhalation to inhalation. The attending anesthetist or another medical person, can thus readily adjust the sharp position of that no-motion transition point, such that it coincides with the diastole of the EKG. In a naturally breathing subject, as shown in traces 204. The region between exhalation and inspiration is broader such that it is easier for the system to await a time when there is overlap of the minimal breathing motion with the diastole of the heartbeat, this being the region of minimal body motion.

The lowest trace 207 in FIG. 2 shows drift of the MEMS IMU output signal baseline over time, represented by the upward slant of the trace. At recurring points of time 203a and 203b, the system controller or the monitor analyzer supplies a trigger signal to the IMU controller to reset the output to zero. In a typical patient under anesthesia, the respiratory rate may vary between 12-20 breaths per minute, corresponding to a respiratory cycle length of 3-5 seconds. The heart rate may range from 60-100 beats per minute, corresponding to a cardiac cycle length of 0.6 to 1 second. As diastole tends to be slightly longer than systole, during roughly half of each cycle the heart would be in a relaxed state and not interfere with resetting of the IMU zero point. As the period of diastole provides a window of opportunity in each cardiac cycle for resetting the baseline reference position of the IMU, the major determinant of the frequency of reset primarily depends on the end of respiration, which will occur approximately once in five seconds. Movements of the rib cage during respiration also contribute more to the cyclic motion than the heartbeat, such that it is more important to find the points of time at which respiration will not introduce motion interfering with baseline resetting, than to pinpoint the diastole in the heartbeat cycle.

Figure 3:
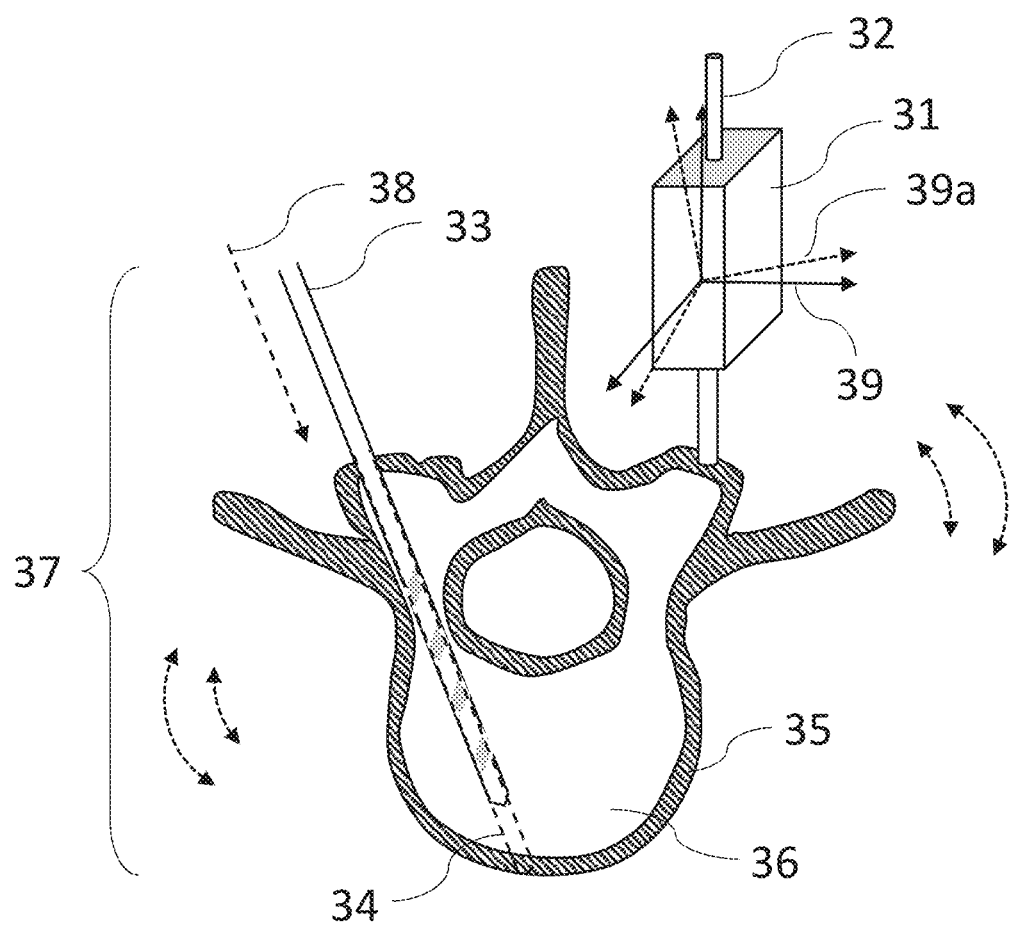
FIG. 3 illustrates the use of a MEMS IMU for keeping track of vibration and tilt of a vertebra, indirectly representing drill bit location, during bone drilling for pedicle screw insertion.

Reference is now made to FIG. 3, illustrating use of the MEMS IMU unit, during robotically controlled drilling of a vertebra in a surgical procedure, to keep track of vertebral tilt and oscillation. These parameters vary as the drill bit traverses from cortical to cancellous bone and can be accurately measured by an IMU. In this exemplary implementation, the drilling is for insertion of a pedicle screw and is performed by a robotic surgical system such as that referred to in FIG. 1. In FIG. 3, the MEMS IMU 31 is shown attached to a K-wire 32, which is embedded in a vertebra 37.

The MEMS IMU has three-dimensional coordinates 39 which are defined by dead reckoning, i.e., by the measurements of its internal MEMS chip. During the drilling process, the drill bit 33 follows the path 34 as calculated in the preoperative plan, first traversing the harder, outer cortical bone 35, then the softer, inner cancellous bone 36. As the drill bit begins to traverse the bone in the direction of arrow 38, the vertebra becomes subject to vibrational and rotational forces caused by the frictional interaction of the bone with the rotating drill bit. These interactions result in predictable and measurable effects on the position and movement of the vertebra. The MEMS IMU 31 is able to register and measure these motions, such as rotation, linear oscillation, and tilt of the vertebra, resulting, for instance, in a positional change represented by the shift in the three-dimensional coordinates 39 to 39a. From these measurements, the control unit can determine the position of the drill bit tip. Based on preselected limits, the controller can then automatically stop the drill bit from penetrating the cortical wall on the anterior side of the vertebra, or measure precisely how far to allow the drill bit to penetrate before halting the drilling. This automatic shut-off capability provides an extra measure of safety and accuracy over the robotic control of the drill bit path as determined in the preoperative plan.

Additionally, the vibrations detected by the IMU can be used to detect the position of the drill in the vertebra, since the IMU has a sufficiently high response time that it can differentiate between the higher frequency vibrations expected when the drill is cutting into cortical bone, as compared to the lower frequency vibrations expected from the softer cancellous bone. The patterns of vibration can then be used to determine whether the drill is following the planned trajectory of the surgical plan.

Figure 4:
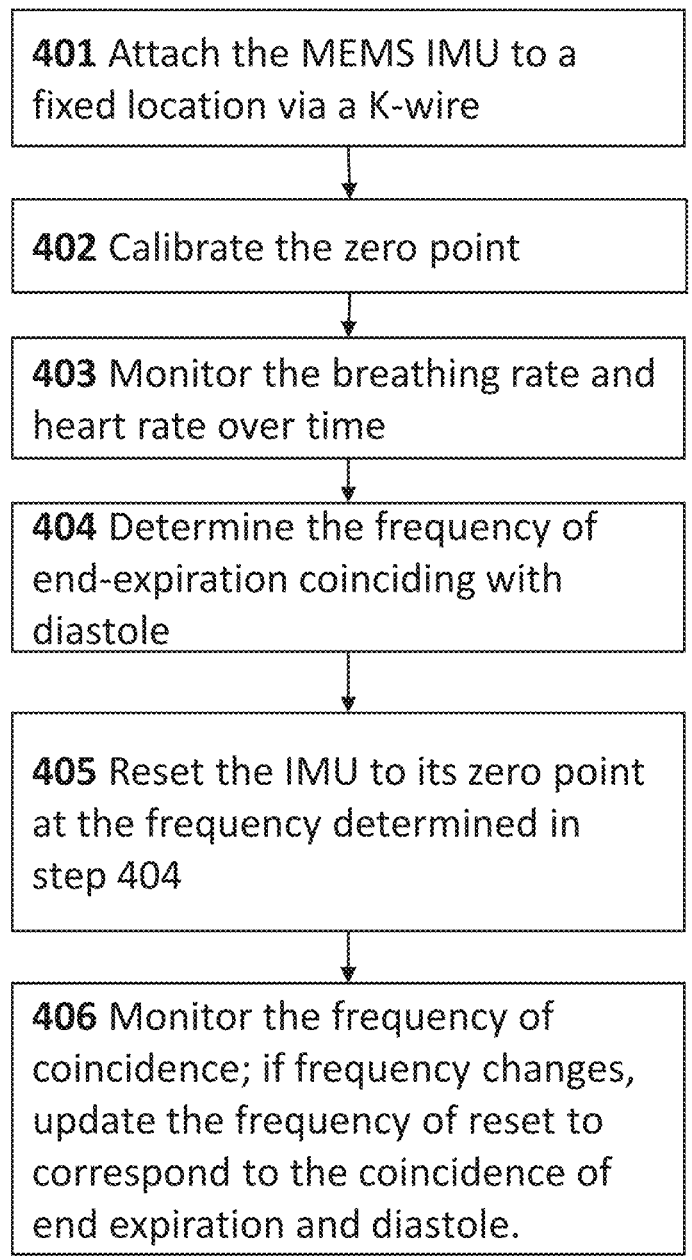
FIG. 4 shows the steps in an exemplary implementation of the methods of the present disclosure.

Reference is now made to FIG. 4, which delineates the steps in an exemplary method of the procedure using the system disclosed in FIGS. 1-3. In step 401, intraoperatively the MEMS IMU is affixed to the bone of a subject undergoing a surgical operation, generally when the subject has been intubated and is under general anesthesia. In this state, the patient's respiration is being controlled by a respirator, at a rate based on the subject's characteristics, which are determined by a medical professional such as an anesthesiologist. EKG leads are attached to the subject to monitor the electrical activity associated with the heart, from which periods of systole and diastole can be determined. In step 402, the zero reference position of the MEMS IMU is set. In step 403, the patient's respiratory rate and heart function are monitored and recorded over a short period of time sufficient to enable the baseline pattern of inspiration/expiration and systole/diastole of the subject in his/her present clinical state. In step 404, the control unit analyzes the baseline pattern, and a determination is made of the points of coincidence between end-expiration and diastole. This information is used by the control unit to calculate the rate at which the MEMS IMU can be reset. The decision about whether to reset the IMU baseline zero at every end-expiration/diastole coincidence, or to do so only every several coincidence occurrences, is dependent on the drift rate of the IMU being used in the system. For a low-drift IMU, the resetting can be performed only every several coincidence events; for an IMU with a higher drift rate, resetting may be necessary at every coincidence event. In step 405, the system resets the IMU output to its zero position, at the frequency determined in step 404. In step 406, the control unit continues to monitor the frequency of coincidence between end expiration and systole. If the frequency changes because of an alteration in the subject's breathing or heart rate, the system updates the reset rate to correspond to the new coincidence rate. Furthermore, in steps of the surgery where higher accuracy may be required, the surgeon may decide to input to the control system an instruction to increase the resetting frequency. The surgical plan itself may incorporate such instructions in its output routine to the system, to reset the IMU more frequently when critical steps of the surgical plan are being executed.

Figure 5:
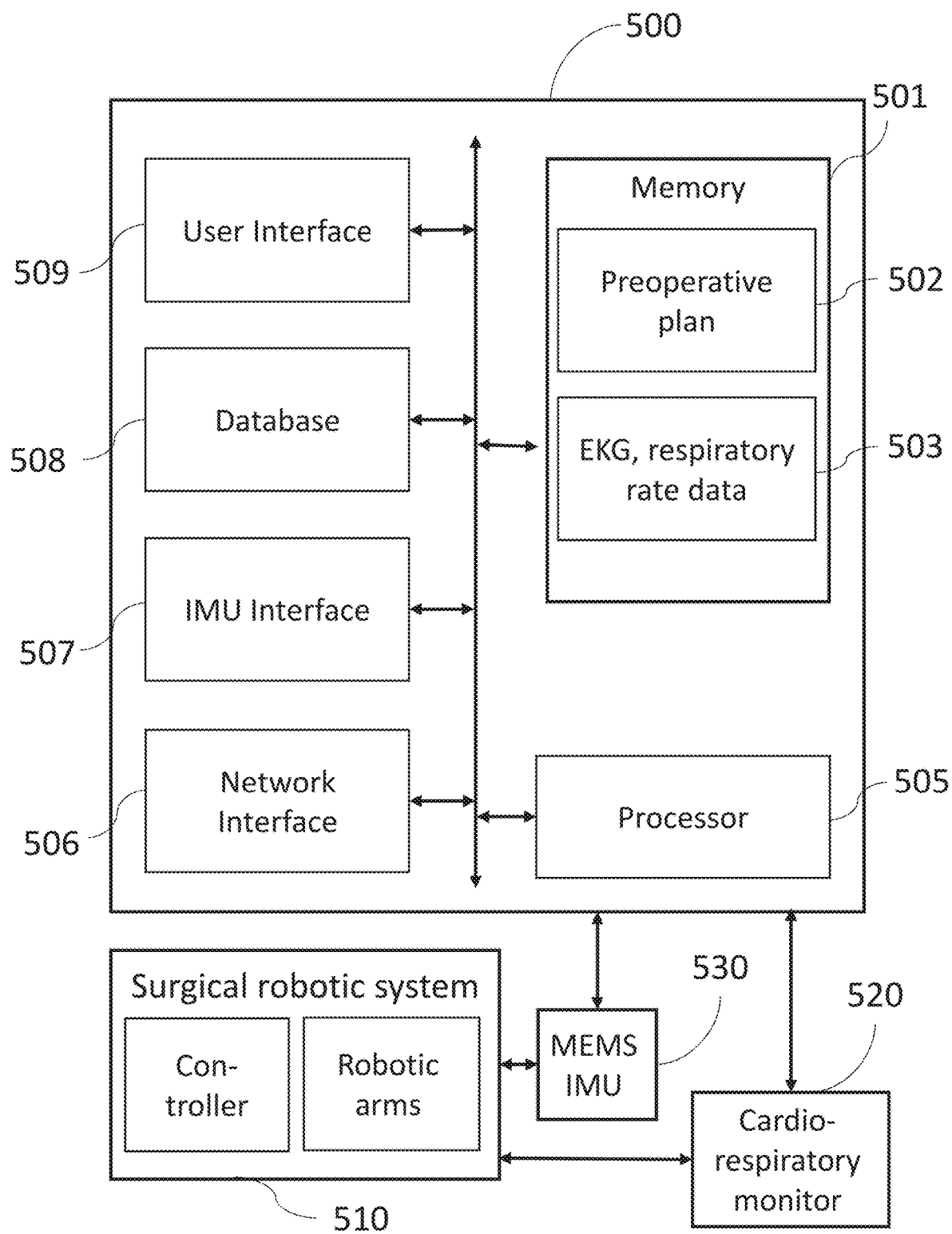
FIG. 5 diagrams the structural components of the control system designed to carry out an exemplary implementation of the disclosed methods.

Reference is now made to FIG. 5, showing the structural components of a typical implementation of the disclosed control system. The control system 500 is in communication with a surgical robotic system 510, with a cardio-respiratory monitor 520, and with an MEMS IMU 530, which function as described in FIGS. 1-4. The control system comprises a memory 501 having in storage at least a preoperative plan 502 and the EKG and respiratory data 503 collected by the cardiorespiratory monitor 520; a processor 505 for analyzing the data; a database of relevant surgical information 508, and interfaces for a user 509, the MEMS IMU 507, and a network 506.

It is appreciated by persons skilled in the art that specific embodiments of the present disclosure are not limited by what has been particularly shown and described hereinabove. Rather the scope of the present disclosure includes both combinations and subcombinations of various features described hereinabove as well as variations and modifications thereto which would occur to a person of skill in the art upon reading the above description and which are not in the prior art.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A surgical robotic system comprising:
an inertial measurement unit (IMU) configured to connect to an anatomical feature of a subject; and
a controller, the controller configured to:
receive a respiratory signal corresponding to a respiratory cycle of the subject, and a heartbeat signal corresponding to a heartbeat cycle of the subject;
determine at least one point in time when:
the respiratory signal represents a position of minimal motion of the subject caused by respiration of the subject; and
the heartbeat signal simultaneously represents a position of minimal motion of the subject caused by heartbeats of the subject; and
generate and send, at the at least one point in time, an electronic signal to the IMU that causes output of the IMU to reset to a reference point, thereby compensating for accumulated drift of the IMU.

2. The surgical robotic system according to claim 1, wherein the at least one point in time when the respiratory signal represents the position of minimal motion of the subject caused by respiration is selected by the controller to be at an end of an expiration phase of the subject's respiratory cycle.

3. The surgical robotic system according to claim 1, wherein the at least one point in time when the heartbeat signal represents the position of minimal motion of the subject caused by heartbeats is selected by the controller to be a diastole period of the subject's heartbeat cycle.

4. The surgical robotic system according to claim 1, wherein the controller is configured to generate and send the electronic signal when an end of an expiration phase of the subject's respiratory cycle and a cardiac diastole period of the subject's heartbeat cycle temporally coincide.

5. The surgical robotic system according to claim 4, wherein a frequency of temporal coincidences of the end of the expiration phase and the cardiac diastole period, at which the controller is configured to reset the reference point of the IMU, is determined by an amount of the accumulated of drift of the IMU.

6. The surgical robotic system according to claim 5, wherein the controller is configured to reset the reference point of the IMU at every occurrence of the temporal coincidence of the end of expiration phase and the cardiac diastole period.

7. The surgical robotic system according to claim 1, wherein the IMU is a microelectromechanical (MEMS) based unit.

8. The surgical robotic system according to claim 1, wherein the IMU is configured to attach fixedly to the anatomical feature of the subject, such that the controller is able to detect changes in at least one of an orientation or a position of the anatomical feature of the subject.

9. The surgical robotic system according to claim 8, wherein the anatomical feature is a bone of the subject, and the controller is configured to use the changes in at least one of the orientation or the position of the bone to determine a type of bone through which a surgical tool is passing.

10. The surgical robotic system according to claim 9, wherein the controller is configured to determine a position in the bone of a surgical drill performing a drilling action on the bone, according to the type of bone.

11. The surgical robotic system according to claim 10, wherein the controller is configured to compare the position of the surgical drill relative to the bone through which it is actually passing, with a position of the surgical drill relative to the bone through which it is passing expected from a surgical plan, to verify whether a surgical procedure is proceeding according to the surgical plan.

12. The surgical robotic system according to claim 8, wherein the controller is configured to instruct the performance of a new registration of the surgical robotic system to the subject if the detected changes in at least one of the orientation or the position of the anatomical feature of the subject exceed respective predetermined threshold levels.

13. The surgical robotic system according to claim 1, wherein the IMU is connected to a bone of the subject using a K-wire.

14. The surgical robotic system according to claim 13, wherein a frequency of vibrations detected by the IMU provides an indication of a type of bone through which a surgical tool generating those vibrations is passing.

15. The surgical robotic system according to claim 14, wherein higher frequency vibrations are interpreted by the controller as indicating passage of the surgical tool through cortical bone, and lower frequency vibrations are interpreted by the controller as indicating passage of the surgical tool through cancellous bone.

16. The surgical robotic system according to claim 15, wherein the IMU is connected to the K-wire in a region which maximizes the amplitude of vibrations arising from a drilling process into the bone.

17. The surgical robotic system according to claim 16, further comprising a second IMU attached to the K-wire, wherein the IMU is attached in a region at which the higher frequency vibrations expected from drilling in cortical bone are maximized, while the second IMU is located in a region where the lower frequency vibrations expected from drilling in cancellous bone are maximized.

18. The surgical robotic system according to claim 14, wherein the controller is configured to use the type of bone indicated to determine the position in the bone of a surgical drill performing a drilling action on the bone.

19. The surgical robotic system according to claim 1, wherein, if the respiratory cycle arises from a subject under general anesthesia, the controller is configured to determine an end of an expiration stage of the subject's respiratory cycle based on external input.

20. A surgical robotic system comprising:
an inertial measurement unit (IMU) configured to connect to an anatomical feature of a subject; and
a controller, the controller configured to:
 receive a respiratory signal corresponding to a respiratory cycle of the subject, and a heartbeat signal corresponding to a heartbeat cycle of the subject;
 determine at least one point in time when:
  the respiratory signal represents a position of minimal motion of the subject caused by respiration of the subject; and
  the heartbeat signal simultaneously represents a position of minimal motion of the subject caused by heartbeats of the subject; and
 generate and send, at the at least one point in time, an electronic signal to the IMU that causes output of the IMU to reset to a reference point, thereby compensating for accumulated drift of the IMU, wherein the controller is configured to determine a pose of the anatomical feature based on the output of the IMU that has been drift-compensated.

* * * * *